(12) United States Patent
Engelhardt et al.

(10) Patent No.: US 10,299,676 B2
(45) Date of Patent: May 28, 2019

(54) METHOD FOR ALIGNING A SYSTEM, AND SYSTEM FOR DETECTING POSITION DATA OF AT LEAST ONE ELEMENT IN THE FRONT REGION OF AN EYE

(71) Applicant: HEIDELBERG ENGINEERING GMBH, Heidelberg (DE)

(72) Inventors: Ralf Engelhardt, Lübeck (DE); Björn Martensen, Lübeck (DE)

(73) Assignee: Heidelberg Engineering GmbH (DE)

( * ) Notice: Subject to any disclaimer, the term of this patent is extended or adjusted under 35 U.S.C. 154(b) by 0 days.

(21) Appl. No.: 14/762,943

(22) PCT Filed: Mar. 28, 2014

(86) PCT No.: PCT/DE2014/100108
§ 371 (c)(1),
(2) Date: Jul. 23, 2015

(87) PCT Pub. No.: WO2014/202047
PCT Pub. Date: Dec. 24, 2014

(65) Prior Publication Data
US 2015/0351630 A1 Dec. 10, 2015

(30) Foreign Application Priority Data
Jun. 19, 2013 (DE) ........................ 10 2013 106 420

(51) Int. Cl.
*A61B 3/11* (2006.01)
*A61B 3/107* (2006.01)
(Continued)

(52) U.S. Cl.
CPC .............. *A61B 3/113* (2013.01); *A61B 3/102* (2013.01); *A61B 3/107* (2013.01); *A61B 3/112* (2013.01); *A61F 9/008* (2013.01)

(58) Field of Classification Search
CPC ......... A61F 9/008; A61B 3/008; A61B 3/113; A61B 3/102; A61B 5/0066; A61B 3/107; A61B 3/112
(Continued)

(56) References Cited

U.S. PATENT DOCUMENTS

| 4,848,340 A | 7/1989 | Bille et al. |
| 2001/0028440 A1 * | 10/2001 | Iwanaga ................. A61B 3/152 351/208 |

(Continued)

FOREIGN PATENT DOCUMENTS

| DE | 102005041710 A1 * | 3/2007 | ............. A61B 3/113 |
| DE | 102009030464 A1 * | 12/2010 | ............. A61F 9/008 |

(Continued)

OTHER PUBLICATIONS

Glaeser, Georg, "Reflections on Spheres and Cylinders of Revolution," Journal for Geometry and Graphics; 1999, pp. 121-139, vol. 3, No. 2, Wien, Austria (in English).

(Continued)

*Primary Examiner* — Boniface N Nganga
(74) *Attorney, Agent, or Firm* — Harness, Dickey & Pierce, PLC

(57) ABSTRACT

A system for detecting position data of an element in the front region of an eye. A first system component continuously detects position changes of the vertex of the cornea of the eye. A second system component directs electromagnetic radiation at topographical structures of the cornea to be ascertained or modified. A control unit includes a processor and memory. Alignment of the first system component with respect to the alignment of the second system component is defined, and the second system component is continuously guided to the respective target position thereof, by the control unit based on the position changes detected by the (Continued)

first system component. Light sources, which illuminate the cornea, are symmetrically disposed around the main axis of the system so that a pattern of reflection points is created on the cornea. The processor determines the current position of the vertex as the center of the reflection points.

10 Claims, 3 Drawing Sheets

(51) Int. Cl.
*A61B 3/10* (2006.01)
*A61F 9/008* (2006.01)
*A61B 3/113* (2006.01)

(58) Field of Classification Search
USPC .................................. 606/4–6; 351/204–212
See application file for complete search history.

(56) References Cited

U.S. PATENT DOCUMENTS

| | | | |
|---|---|---|---|
| 2002/0013576 A1* | 1/2002 | Gray | A61F 9/00804 |
| | | | 606/5 |
| 2002/0173778 A1* | 11/2002 | Knopp | B23K 26/04 |
| | | | 606/5 |
| 2005/0278004 A1 | 12/2005 | Steinert et al. | |
| 2008/0055543 A1* | 3/2008 | Meyer | A61B 3/102 |
| | | | 351/205 |
| 2009/0275929 A1* | 11/2009 | Zickler | A61B 3/113 |
| | | | 606/5 |
| 2011/0069279 A1* | 3/2011 | Hacker | A61B 3/102 |
| | | | 351/221 |
| 2011/0149241 A1 | 6/2011 | Dai | |
| 2011/0273669 A1* | 11/2011 | Abitbol | A61B 3/1015 |
| | | | 351/212 |
| 2013/0039557 A1 | 2/2013 | Wei et al. | |

FOREIGN PATENT DOCUMENTS

| | | | |
|---|---|---|---|
| DE | 10-2009-030466 A1 | 1/2011 | |
| DE | 102009030466 A1 * | 1/2011 | A61B 3/152 |
| EP | 1985269 A1 | 10/2008 | |
| JP | 2000139996 A | 5/2000 | |
| JP | 2005087548 A | 4/2005 | |
| JP | 2010261858 A | 11/2010 | |
| JP | 2011516187 A | 5/2011 | |
| WO | WO-9316631 A1 | 9/1993 | |
| WO | WO-2011-156721 A1 | 12/2011 | |

OTHER PUBLICATIONS

International Search Report (in English and German) for PCT/DE2014/100108, dated Aug. 25, 2014; ISA/EP.
International Preliminary Report on Patentability (Chapter II of the Patent Cooperation Treaty) (in German) for PCT/DE2014/100108, Completed Jun. 5, 2015; IPEA/EP.
Notice of Reasons for Refusal dated Aug. 29, 2017 (with English translation) regarding Japanese Patent Application No. 2016-520280 (13 pages).
Notice of Reasons for Refusal dated Apr. 25, 2018 (with English translation) regarding Japanese Patent Application No. 2016-520280 (13 pages).

* cited by examiner

METHOD FOR ALIGNING A SYSTEM, AND SYSTEM FOR DETECTING POSITION DATA OF AT LEAST ONE ELEMENT IN THE FRONT REGION OF AN EYE

CROSS-REFERENCE TO RELATED APPLICATIONS

This application is a National Stage of International Application No. PCT/DE2014/100108, filed Mar. 28, 2014. This application claims the benefit and priority of German application 10 2013 106 420.5, filed Jun. 19, 2013. The entire disclosures of the above applications are incorporated herein by reference.

BACKGROUND

This section provides background information related to the present disclosure which is not necessarily prior art.

Technical Field

The invention relates to a method for aligning a system for detecting position data of at least one element in the front region of an eye, wherein the system comprises at least one first system component and a second system component. The invention further relates to a system for detecting such position data.

Discussion

Such a method and such a system are known from DE 10 2009 030 466 A1. In preparation for refractive laser treatment of the eye, initially the current data of physical variables influencing the imaging of the eye is collected there, and subsequently the eye defects to be corrected are determined. These corrections for the imaging process of the eye must then be converted into a treatment procedure, which results in a local ablation of corneal tissue, for example, so as to generate an appropriately modified shape of the cornea. For a proper correction, it is indispensable for the diagnostic data and therapeutic data to relate to a shared geometric reference point. According to DE 10 2009 030 466 A1, the vertex of a cornea has been found to be an advantageous reference point, which is to say the location of the maximum elevation of the surface of the cornea, at which the ascertained data sets are recorded.

During the examination or the treatment of the front region of the eye by way of chronologically serial diagnostic and/or treatment processes, which generally consist of multiple steps, the oculomotor system impairs the integrity and continuity of the process, be it arbitrarily or involuntarily, consciously or unconsciously. While subsequent corrections and/or tracking are possible for diagnostic data, they contain inhomogeneous information densities in the case of strong movements, resulting in local inaccuracies. For treatment systems, subsequent correction is not practical.

SUMMARY OF THE INVENTION

It is therefore an object of the invention to provide a method for aligning a system and a system for detecting position data of at least one element in the front region of an eye, which ensure continuous adaptation to movements of the eye so as to reliably generate diagnostic data sets and/or data sets for material changes.

The method according to the invention in accordance with the species mentioned at the outset provides a continuous detection of position changes of least one distinct location and/or at least one distinct structure on the cornea and/or on the region of an eye located behind the cornea by aligning the first system component with this location or with this structure, and further includes directing electromagnetic radiation at topographical structures of the cornea to be ascertained or to be modified by aligning the second system component, characterized in that the alignment of the first system component with respect to the alignment of the second system component is defined, and the second system component is continuously guided to the respective target position thereof based on the position changes detected by the first system component. According to the invention, the detected information allows continuous tracking of the diagnostic and/or treatment system.

According to an advantageous embodiment of the invention, one of the distinct locations is the vertex of the cornea, and thus the position changes of the vertex are detected. The calculated vertex position contains information about the translation of the entire eye ball in the application area, as it is created, for example, by the incomplete fixation of the head. If additionally further structures of the eye are evaluated, as is described below, additional degrees of freedom can be determined.

Detecting the vertex position is already known from DE 10 2009 030 466 A1. According to a further preferred embodiment of the invention, however, it is now provided here to illuminate the cornea using at least one light source, so that reflections are created on the cornea, wherein the current position of the vertex is then determined from the positions of the reflections.

One possible measure according to the invention provides for the position change of the reflections to be used directly for guiding the second system component to the respective target position thereof.

However, on the other hand it also has advantages if multiple light sources are disposed symmetrically around the main axis of the system. It is then possible to use the positions of the reflection points caused by the light sources on the eye to determine an at least approximate position of the vertex. This is because a symmetrical arrangement of the light sources around the main axis of the system creates a symmetrical pattern of reflection points, wherein an origin of symmetry of the arrangement of the reflection points at least approximately corresponds to the position of the vertex. The origin of symmetry can be determined with the aid of a convolution. Such a method can be implemented very quickly and without major complexity.

The vertex can thus be determined with sufficient precision by way of the reflection points. However, a parallax error arises if the vertex is not located on the optical main axis. This parallax error can be corrected if the radius of the curvature of the cornea is known. Human corneas do not vary significantly in the radius of curvature; they exhibit values between 7 mm and 9 mm, so that the parallax correction is relatively good if it is determined for a sphere having a diameter of 8 mm.

To implement such a procedure, it is advantageously further provided in the method according to the invention for the position of a further one of the distinct locations or of a further one of the distinct structures on the cornea and/or on the region of an eye located behind the cornea relative to the vertex to be determined, wherein it is provided in particular that the further distinct structure is the pupil of the eye.

For this purpose, it is also possible to include the position of the reflection, or the positions of the reflections, in the determination of the geometry of the pupil.

Moreover, rotational position changes—also referred to as cyclotorsion—of the eye can be ascertained from position changes of the further distinct location and/or the further distinct structure on the cornea and/or on the region of an eye located behind the cornea relative to the vertex. By evaluating the pupil position with respect to the vertex position, the tilting of the eye ball and the fixation capability during a diagnostic and/or treatment process are ascertained.

This means that fixation can be monitored based on the rotational position changes of the eye, so that optionally a loss of fixation is noticed. Fixation in ophthalmology refers to the deliberate observation of an object in the area outside the eye, which normally takes place with the retinal point having the highest resolution, this being the fovea centralis. This point conveys the "straight ahead" directional sensation and thus represents the main physiological viewing direction of the eye.

According to one variant according to the invention, it may be provided in the method that the quality of the cornea surface and/or the condition of the precorneal film on the surface of the cornea are ascertained based on the quality of the reflection points. While tracking, if it is carried out in accordance with the present invention, is relatively precise and robust to begin with, it may result in smaller jumps, for example when the precorneal film is disrupted. These inaccuracies can be prevented by a quality check.

The second system component can now be used to record one- or multi-dimensional deep sectional images. These have a known position relative to the vertex.

The vertex is newly determined in each case based on the current camera image. The movement in the camera image can be determined based on the reflection points relative to the first camera image, so that a consideration in the calculation of the scanner coordinates can take place. The movement in the camera image is determined based on other structures in the entire image in one section, or in multiple sections, relative to the first camera image and considered in the calculation of the scanner coordinates.

In this way, arbitrary scan patterns, such as rasters or meridians, can now be recorded. In particular, it is ensured that meridian sections extend through the vertex, and a refraction correction can take place in one plane. Topographies can be recorded without subsequent lateral movement tracking. Axial movements are easy to calculate, since all deep sections have a common point, in particular in the case of meridian scan patterns.

It is therefore provided to determine axial position changes based on differences between deep sections recorded at the same position in the geometry of the eye on the frontal plane. The position of the vertex can be checked at any time based on a deep sectional image that is recorded at this position.

The invention further relates to a system for detecting position data of at least one element in the front region of an eye.

In this system, changes can be made to endogenous and/or implanted material, such as an intraocular lens, using the second system component.

A third system component can be provided as an alternative for this purpose, wherein the alignment of the first and second system components relative to each other and to the third system component is defined, and the positioning of the third system component is continuously regulated to the respective target position based on the position changes detected by the first and second system components.

Using the ascertained position information, the activation and deactivation of the second system component, and optionally of the third system component, can be regulated. It is also possible to regulate the recording and discarding of measured values.

BRIEF DESCRIPTION OF THE DRAWINGS

The drawings described herein are for illustrative purposes only of selected embodiments and not all possible implementations, and are not intended to limit the scope of the present disclosure.

The invention will be described in more detail hereafter based on the accompanying drawings. In the drawings.

Corresponding reference numerals indicate corresponding parts throughout the several views of the drawings.

DETAILED DESCRIPTION OF THE PREFERRED EMBODIMENTS

Example embodiments will now be described more fully with reference to the accompanying drawings.

Figure 1:
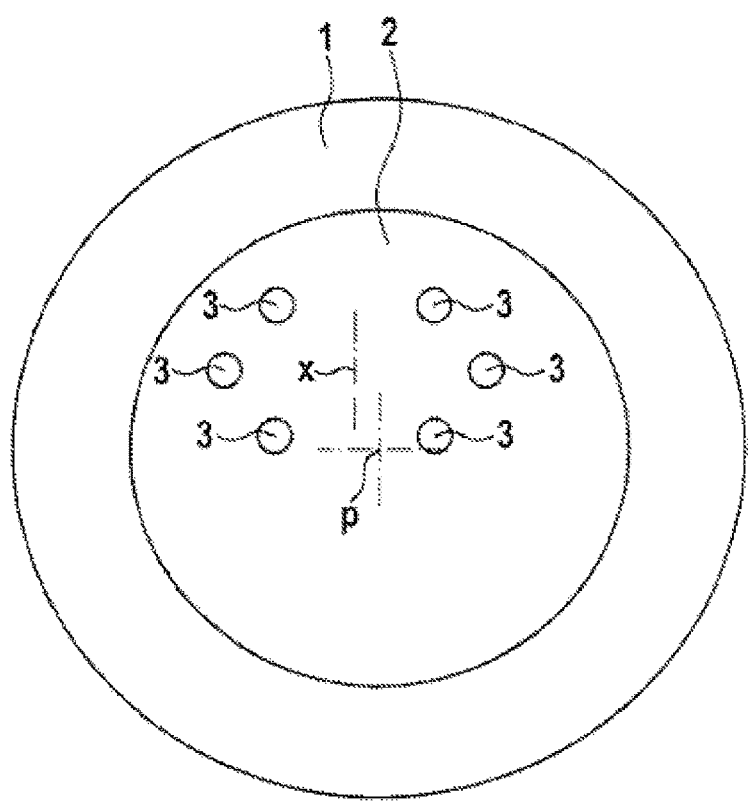
FIG. 1 shows a schematic view of an eye, wherein reflection points have been generated on the cornea by external light sources.

FIG. 1 shows a schematic illustration of the front region of a human eye, in which a pupil 2 is surrounded by an iris 1. p denotes the center of the pupil. In a system according to the invention, light sources are symmetrically disposed around the main axis of the diagnostic and/or treatment system, resulting in a pattern of reflection points 3. The center x of the reflection points 3 corresponds approximately to the vertex of the eye. The position of the vertex of the eye is also dependent on the fixation and fixation axis. If the position of the pupil 2 or of the pupil center p in relation to the center x of the reflection points 3 is tracked, fixation can be monitored, and a loss of fixation resulting in misalignment of the eye can be detected.

This monitoring is useful in particular for systems that ascertain geometric information of the front region of the eye sequentially during a time interval, for example by way of individual deep sections, since in this way information about the alignment of the eye in the sequence is available. The vertex position of the front region of the eye can also be determined for complex geometries of the light sources generating the reflection points on the diagnostic and/or treatment system by tracking of the beam, as it is also carried out for the generation of 3D computer graphics. A representation can be found in Reflections on Spheres and Cylinders of Revolution, Georg Glaeser, Journal for Geometry and Graphics, Volume 3 (1999), No. 2, 121-139.

Figure 2:
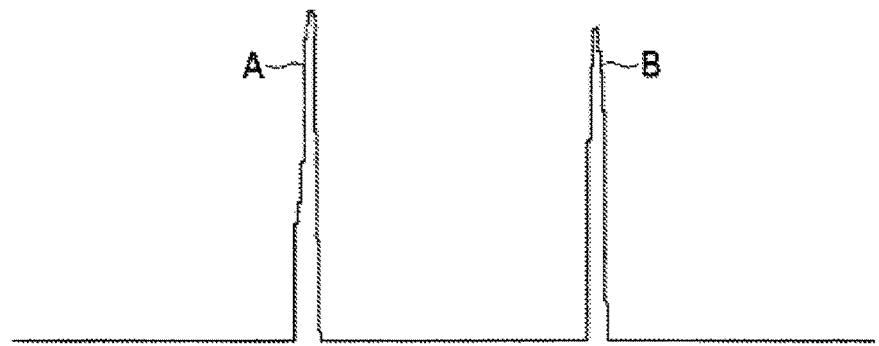
FIG. 2 shows a one-dimensional sectional illustration of the reflection points.
Figure 3:
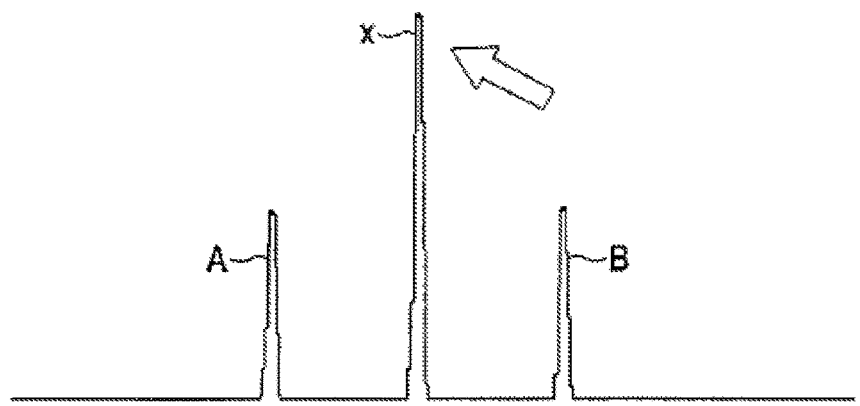
FIG. 3 shows the convolution of the image of FIG. 2 with the inverted image.
Figure 4:
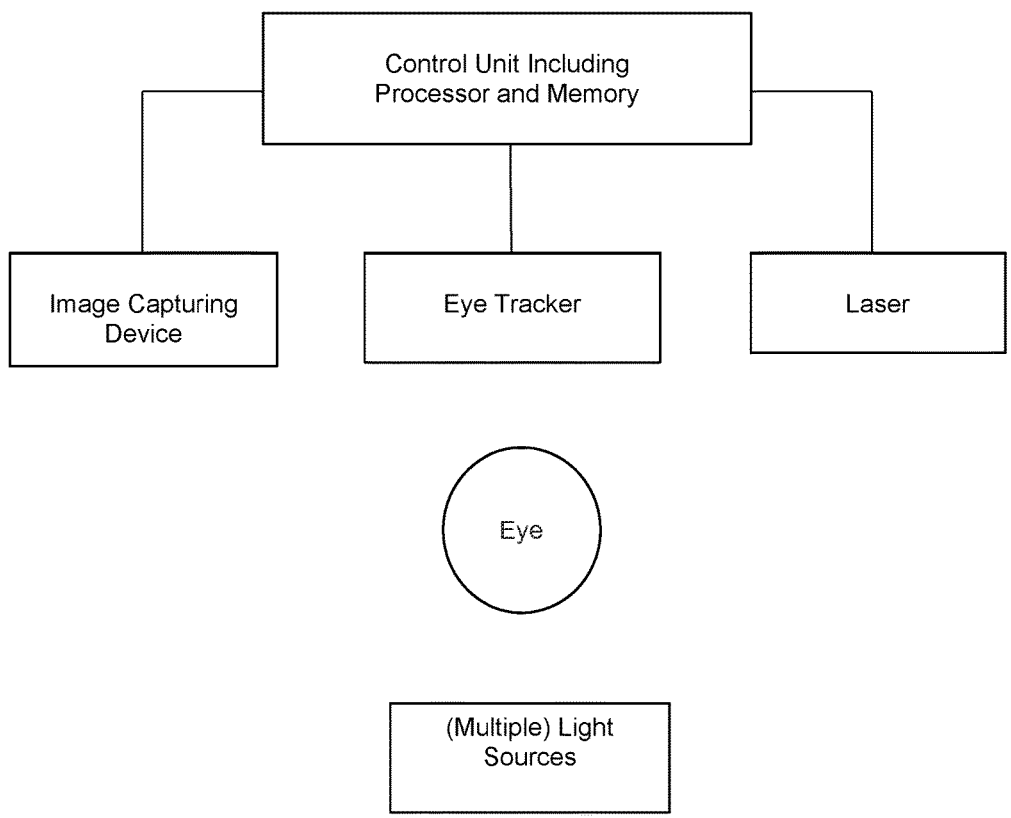
FIG. 4 illustrates a system in accordance with the present teachings for detecting position data of at least one element in the front region of an eye.

FIG. 2 shows a one-dimensional sectional illustration of the reflection points, more specifically based on the example of the signal peaks A and B. It goes without saying that additional reflection points are to be represented by similar signal peaks. As a result of the convolution of the image of FIG. 2 with the inverted image, the center x of the reflection points 3 (FIG. 1) is ascertained, as is shown in FIG. 3, which corresponds approximately to the vertex of the cornea or of the eye.

The features of the invention disclosed in the above description, in the drawings and in the claims can be essential for the implementation of the invention either alone or in any arbitrary combination with each other.

The foregoing description of the embodiments has been provided for purposes of illustration and description. It is not intended to be exhaustive or to limit the invention. Individual elements or features of a particular embodiment are generally not limited to that particular embodiment, but, where applicable, are interchangeable and can be used in a selected embodiment, even if not specifically shown or described. The same may also be varied in many ways. Such variations are not to be regarded as a departure from the invention, and all such modifications are intended to be included within the scope of the invention.

The invention claimed is:

1. In a system for detecting position data of at least one element in a front region of an eye, the system including: at least one first system component designed to continuously detect position changes of a vertex of a cornea of the eye; a second system component that directs electromagnetic radiation at topographical structures of the cornea to be ascertained or to be modified; and a control unit including a processor and a memory; wherein an alignment of the first system component with respect to an alignment of the second system component being defined, and the second system component being continuously guided to a respective target position thereof by the control unit based on the position changes detected by the first system component, wherein the improvement comprises:

wherein light sources, which illuminate the cornea, are symmetrically disposed around a main axis of the system, so that a pattern of reflection points is created on the cornea, the processor determining a current position of a vertex as the center of the reflection points;

wherein the second system component records one- or multi-dimensional deep sectional images;

wherein axial position changes are determined from differences between deep sectional images recorded at a same position in a geometry of the eye on a frontal plane; and wherein the system sequentially obtains geometric information of the front region of the eye during a time interval by way of the deep sectional images to gather information regarding alignment of the eye.

2. In the system according to claim 1, further comprising a third system component, an alignment of which with respect to the first system component and the second system component is defined, and which is guided by the control unit to a respective target position thereof based on detected position changes to modify endogenous and/or implanted material.

3. In the system according to claim 1, wherein a point of origin of the pattern of reflection points corresponds at least approximately to the position of the vertex.

4. In the system according to claim 3, wherein the point of origin is determined with the aid of a convolution.

5. In the system according to claim 1, wherein the position of a further distinct location and/or of a further distinct structure on the cornea and/or on a region of the eye located behind the cornea relative to the vertex is determined.

6. In the system according to claim 5, wherein the further distinct structure is a pupil of the eye.

7. In the system according to claim 6, wherein a geometry of the pupil is derived from a position of a reflection or positions of the reflections.

8. In the system according to claim 4, wherein position changes of a further distinct location and/or of a further distinct structure on the cornea and/or on a region of the eye located behind the cornea relative to the vertex are used to ascertain rotational position changes of the eye.

9. In the system according to claim 8, wherein fixation is monitored based on the rotational position changes of the eye, and a loss of fixation is noticed.

10. In the system according to claim 1, wherein a quality of the cornea surface and/or a condition of a precorneal film on a surface of the cornea are ascertained based on the quality of the reflection points.

* * * * *